US008768722B2

(12) United States Patent
Cho

(10) Patent No.: US 8,768,722 B2
(45) Date of Patent: Jul. 1, 2014

(54) DRUG FRACTIONAL SYSTEM USING GENERIC GROUP CODE AND UNIVERSAL DRUG NUMBER AND METHOD THEREOF

(76) Inventor: Young-Whan Cho, Paju-Si (KR)

( * ) Notice: Subject to any disclaimer, the term of this patent is extended or adjusted under 35 U.S.C. 154(b) by 918 days.

(21) Appl. No.: 12/591,129

(22) Filed: Nov. 10, 2009

(65) Prior Publication Data

US 2010/0250545 A1 Sep. 30, 2010

(30) Foreign Application Priority Data

Mar. 27, 2009 (KR) .................. 10-2009-0026551

(51) Int. Cl.
*G06Q 50/00* (2012.01)
(52) U.S. Cl.
USPC .................................. 705/2; 705/3
(58) Field of Classification Search
USPC ........................................................ 705/2, 3
See application file for complete search history.

(56) References Cited

U.S. PATENT DOCUMENTS

| 7,706,915 B2* | 4/2010 | Mohapatra et al. | 700/231 |
| 2002/0087554 A1* | 7/2002 | Seelinger | 707/10 |
| 2003/0078911 A1* | 4/2003 | Haskell et al. | 707/2 |
| 2004/0172285 A1* | 9/2004 | Gibson | 705/2 |
| 2005/0108044 A1* | 5/2005 | Koster | 705/2 |
| 2007/0124171 A1* | 5/2007 | Benfield | 705/2 |

* cited by examiner

*Primary Examiner* — Lena Najarian
(74) *Attorney, Agent, or Firm* — Maxon IP LLC.; Justin H. Kim

(57) ABSTRACT

A drug classification system using a generic group code and a universal drug number is developed to determine whether the drug comprises a single formulation or a composite formulation using the generic group code, understands an administration type, dose and/or formulation type of the drug, registers a universal drug number for the drug in association with the generic group code, traces back the generic group code from the universal drug number, and identifies a company name and a trade name of the drug which in turn rapidly and easily recognizes the drug; and, in addition, a drug classification method using the same. The system may manage the generic group code and the universal drug number in association with the company code, thereby enabling quick and exact management of drug information.

12 Claims, 6 Drawing Sheets

Fig. 4

DRUG FRACTIONAL SYSTEM USING GENERIC GROUP CODE AND UNIVERSAL DRUG NUMBER AND METHOD THEREOF

BACKGROUND OF THE INVENTION

1. Field of the Invention

The present invention relates to a drug fractional system using generic group codes and universal drug numbers and a method thereof. More particularly, the drug registered with the generic group codes in the system is able to determine whether it is a single component or composite formulation. The universal drug numbers are also registered corresponding to the generic group codes for crosschecking. So that, an individual drug is easily identified and recognized the maker's name and a trade name.

2. Related Prior Art

As well known in related arts, a drug is a chemical substance which is edible, applicable and/or injectable to organisms including human beings, in order to cure diseases, to remedy injuries, and/or to prevent the disease.

For pharmaceutical applications in which such drugs and/or chemical substances are mostly managed, a number of information including, for example, constitutional components of a drug, interaction between two or more drugs, side effects, instruction for administration of medicines, etc. are required. Especially, the physicians and/or pharmacists wish to get information of the recent medical news and advanced medicines.

However, such medicines are generally divided into numerous types of drugs such as anti-diaarhoeal drugs, analgesics, antibiotics, neuroleptics, and the like, based on medical efficacies thereof. Although about 6,000 drug species for medical application and about 3,400 drug species for surgical application have been currently known, even physicians or pharmacists sometimes do not understand quite well about various efficacies and/or constitutional ingredients of all of these medicines.

Meanwhile, since those are not skilled in the art generally lack detailed knowledge of medicines and may not understand specific efficacies of a drug only with name thereof. As disclosed above, since there are many kinds of drugs available, problems of misunderstanding efficacies of such drugs may be entailed, leading to serious accidents caused by abuse, misuse and/or adverse effects of medicines.

According to Public Notice No. 2000-33 of the Korean Ministry of Health and Welfare, "Principal Drug Component Code Index" was published on 1 Jul., 2000, in complying with provisions of Article 24, Item 3 of Enforcement Decree of National Health Insurance Act and Article 8, Item 2 of National Health Care Payment Standard Regulation.

Following this, Korean Food and Drug Administration (KFDA) progresses a project to prepare Standard Code for Medical Components. The foregoing principal drug component code was revised twice with additional components and about 6,200 items are recoded in the principal drug component code in January, 2004.

The principal drug component code managed by KFDA has been set in nine-digit number (N: number, A: English alphabet)

1111-11-A-AA (e.g., 2243-01-ATB)

However, such existing code encounters the following problems:

Classification of medicines based on the component code is executed by sorting whether a drug comprises a single component or a composite formulation (containing at least two components) and endowing a serial number as the code to each of 4,500 single formulations and 1,400 composite formulations.

Briefly, the first four-digit numeral means a component, the next two-digit numeral represents content thereof, and the last three alphabets means a formulation containing the component.

Accordingly, a single formulation may be easily found during search of a drug but it is impossible to search a composite formulation with the first four-digit numeral. Random comparison of composite formulations with the code is a very hard and difficult work. In particular, different codes are often endowed to the same item or different items sometimes have the same code, thus reducing overall consistency in code definition.

Especially, for a composite formulation containing, e.g., about 20 kinds of vitamins, a correct code of the formulation is substantially not searched with the generic principal component (that is, vitamin).

Due to the foregoing problem, the principal drug component code index was abolished on Apr. 26, 2004 (Public Notice No. 2004-27 of Ministry of Health and Welfare). Afterward, the foregoing code index is under management of Health Insurance Review and Assessment Service ("HIRAS") additional items, to which some items are added.

Accordingly, it was known that the conventional component code composed of serial numbers and alphabets with nine digits is insufficient to classify numerous and various medicines and has problems of not simply or correctly searching desired drugs.

In every month, about 1,000 trade names of medicaments are newly registered in Korea. Therefore, owing to a great amount of information for drugs under management, search of a particular drug using a drug name or trade name thereof is economically disadvantageous and encounters a problem of delayed registration of drug information. In addition, if the current system for classification of drugs using drug names is continued, the number of digits to express a drug code is continuously increased. Consequently, further additional medicines cannot be managed with the current drug codes.

SUMMARY OF THE INVENTION

The present invention is directed to solving conventional problems as described above and an object of the present invention is to provide a drug fractional (or classification) system using a component code (hereinafter, referred to as "generic group code") and a component serial number (hereinafter, referred to as "universal drug number"), capable of determining whether a drug comprises a single formulation or a composite formulation using an generic group code, understanding administration type, dose and/or formulation type of the drug, registering a universal drug number of the drug in association with the generic group code, tracing back the generic group code from the universal drug number, and identifying a company name and a trade name of the drug and, in addition, a drug classification method using the same.

According to an exemplary embodiment of the present invention to accomplish the above purposes, there is provided a drug classification system, including: a user equipment 2 that connects to a drug classification server 4 through a data network, displays information in association with generic group codes, which are pre-registered in the server by applying known generic group codes and/or universal drug numbers, displays a detailed drug name in associated with the known generic group codes or, otherwise, inputs a specific drug name into the server in order to display corresponding generic group codes and universal drug numbers; a drug classification server 4 that automatically assigns a generic group code and a universal drug number corresponding to a new drug information, registers the assigned generic group code and universal drug number corresponding to the drug information, combines a company code into the universal drug number, receives an information regarding a certain generic group code, universal drug number or drug name, and then, extracts a corresponding information from the registered drug-related information, and transmits the extracted information to the user equipment 2; and a database 6 to store drug-related information.

The user equipment 2 in the drug classification system using a generic group code and a universal drug number is preferably cable/radio telecommunication terminal equipment.

The generic group code registered in the drug classification server 4 may be a nine-digit code in which an information indicating whether a given drug comprises a single component or a composite formulation, as well as another information about administration type, dose and formulation type of the same drug are recorded.

The universal drug number registered in the drug classification server 4 may be an inherent serial number associated with the corresponding generic group code and, if given drugs are indicated by the same universal drug number, they also have the same generic group code.

Preferably, the present invention provides a drug classification system using a generic group code and a universal drug number, wherein a drug classification server 4 includes:

a drug information registry that newly registers a drug information, which is received from a key input part connected to a drug classification server 4, to a database in order to view (or read) the information;

a generic group code input part installed in the drug information registry to receive overall drug information including information about a single component or composite formulation type drug;

an universal drug number input part installed in the drug information registry to receive a universal drug number in association with a generic group code for the single component or composite formulation type drug;

an automatic generic group code assigning part that automatically assigns a head rank information of the generic group code, depending on the single component or composite formulation type drug, from a new component information when this component information is inputted by the generic group code input part, then, combines the assigned information with a following rank information of the generic group code, which is pre-inputted, in order to automatically create a new unique generic group code;

a universal drug number assigning part that creates a universal drug number matching to the unique generic group code, when the unique generic group code is newly created;

a database for storing generic group code information in association with corresponding universal drug number information, with respect to a plurality of drugs; and a control part that operates individual processors installed in the drug classification server 4, which in turn, controls drug information, creation of new generic group codes, creation of new universal drug numbers and/or registration thereof.

The drug classification server 4 may further include: a data sink that receives an identification information, and another information about a generic group code, a universal drug number and/or a drug name from the user equipment 2; a data transfer part that extracts a drug information corresponding to the generic group code, universal drug number and/or drug name received from the user equipment 2, then, transmits the extracted information to the user equipment 2; and an authentication center (AUC) that certifies identity of a user according to the identification information received from the user equipment 2.

The foregoing database 6 may consist of a generic group code storage part and a universal drug number storage part wherein both storage parts are interconnected.

According to the inventive drug classification system, the generic group code assigned by the drug classification server 4 is preferably composed of nine digits and, if a drug comprises a single component, the first digit of the generic group code assigned to the drug is the first alphabet of an original name of the component.

According to the inventive drug classification system, if a drug comprises a single component, the second and third digits of the generic group code assigned to the drug by the drug classification server 4 may be numeral codes converted from the second and third alphabets of an original name of the component, respectively.

According to the inventive drug classification system, if a drug comprises a single component, the fourth digit of the generic group code assigned to the drug by the drug classification server 4 may be an inherent serial number assigned by collecting all of drugs having the same three digits (from the first to the third digit) of the generic group code as those of the foregoing single component drug, then, uniquely endowing a serial number to each of the drugs.

According to the inventive drug classification system, if several drugs have the same four digits (from the first to the fourth digit) of the generic group code thereof assigned by the drug classification server 4, all of these drugs may substantially comprise the same components.

According to the inventive drug classification system, if a drug comprises a composite formulation, the first digit of the generic group code assigned to the drug by the drug classification server 4 may be the first alphabet of an original name of the first component contained in the formulation type drug.

According to the inventive drug classification system, if a drug comprises a composite formulation, the second digit of the generic group code assigned to the drug by the drug classification server 4 may be the first alphabet of an original name of the last component contained in the formulation type drug.

According to the inventive drug classification system, if a drug comprises a composite formulation, the third digit of the generic group code assigned to the drug by the drug classification server 4 may be the number of components contained in the formulation type drug.

According to the inventive drug classification system, if a drug comprises a composite formulation, the fourth digit of the generic group code assigned to the drug by the drug classification server 4 may be an inherent serial number assigned by collecting all of drugs having the same three digits (from the first to the third digit) of the generic group code as those of the foregoing composite formulation drug, then, uniquely endowing a serial number to each of the drugs.

According to the inventive drug classification system, regardless of whether the drug comprises a single component or a composite formulation, the fifth digit of the generic group code assigned to the drug by the drug classification server 4 may be a symbol expressing an administration type of the drug.

According to the inventive drug classification system, regardless of whether the drug comprises a single component or a composite formulation, the sixth and seventh digits of the generic group code assigned to the drug by the drug classification server 4 may be a symbolic code expressing a dose of the drug.

According to the inventive drug classification system, regardless of whether the drug comprises a single component or a composite formulation, the eighth and ninth digits of the generic group code assigned to the drug by the drug classification server 4 may be a symbolic code expressing a formulation type of the drug.

According to another exemplary embodiment of the present invention to accomplish the above purposes, there is provided a drug classification method, including:

a first stage of inputting component information by a server manager;

a second stage of assigning a generic group code according to the component information;

a third stage of assigning a universal drug number to match with the generic group code when the generic group code is assigned;

a fourth stage of interconnecting between the generic group code and the universal drug number by a drug classification server, when the universal drug number is assigned;

a fifth stage of inputting a given generic group code, universal drug number or drug name into the drug classification server through a user equipment;

a sixth stage of extracting a component information corresponding to the given generic group code, universal drug number or drug name by the drug classification server and displaying the extracted information on the user equipment;

a seventh stage of determining whether a signal for selecting the generic group code is received from the user equipment by the drug classification server; and an eight stage of extracting the drug information corresponding to the generic group code by the drug classification server and displaying the extracted information on the user equipment, when the generic group code is received.

According to the foregoing inventive drug classification method, the second stage includes: determining whether a drug comprises a single component or a composite formulation by the drug classification server according to the component information input by a manager; registering a corresponding component name of the drug and automatically assigning the first four digits of the generic group code for the drug by the drug classification server; and, when the manager inputs certain administration type, dose and formulation type related information, automatically combining the inputted information with pre-registered codes regarding administration type, dose and formulation type information, then, completing a final nine-digit generic group code of the drug.

As disclosed above, a drug classification system using a generic group code and a universal drug number and a drug classification method using the same according to the present invention may clearly express a drug while favorably abbreviating a name thereof, so as to enable recognition of the drug by others. The present invention also has beneficial features in that two or more components are comparable to one another using the first four digits of each generic group code thereof, substances for management in a database are considerably reduced, a drug is easily registered, and components may be statistically managed. In addition, the drug classification system may manage the generic group code and the universal drug number in association with a company code, thereby enabling quick and exact management of drug information.

BRIEF DESCRIPTION OF THE DRAWINGS

Figure 4:
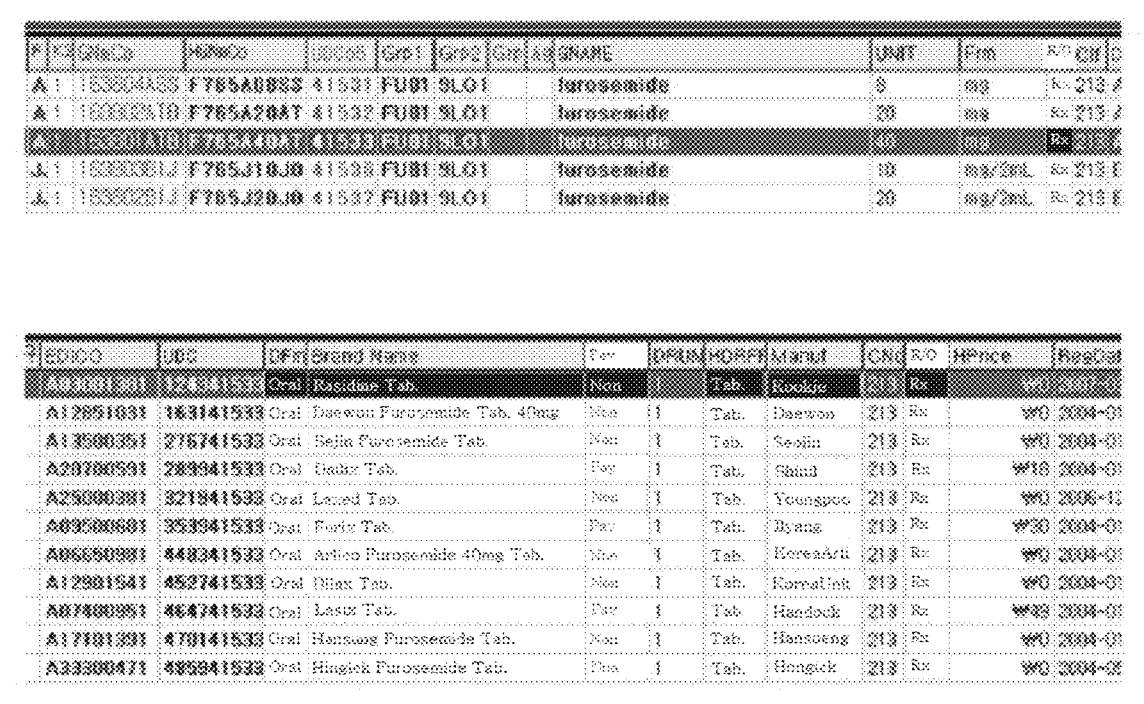

FIG. 4 shows web screens displaying interconnection outputs of generic group codes and universal drug numbers by the drug classification system using a generic group code and a universal drug number according to an exemplary embodiment of the present invention.

DETAILED DESCRIPTION OF THE PREFERRED EMBODIMENT

Hereinafter, the present invention will be described in greater detail with reference to accompanying drawings.

Figure 1:
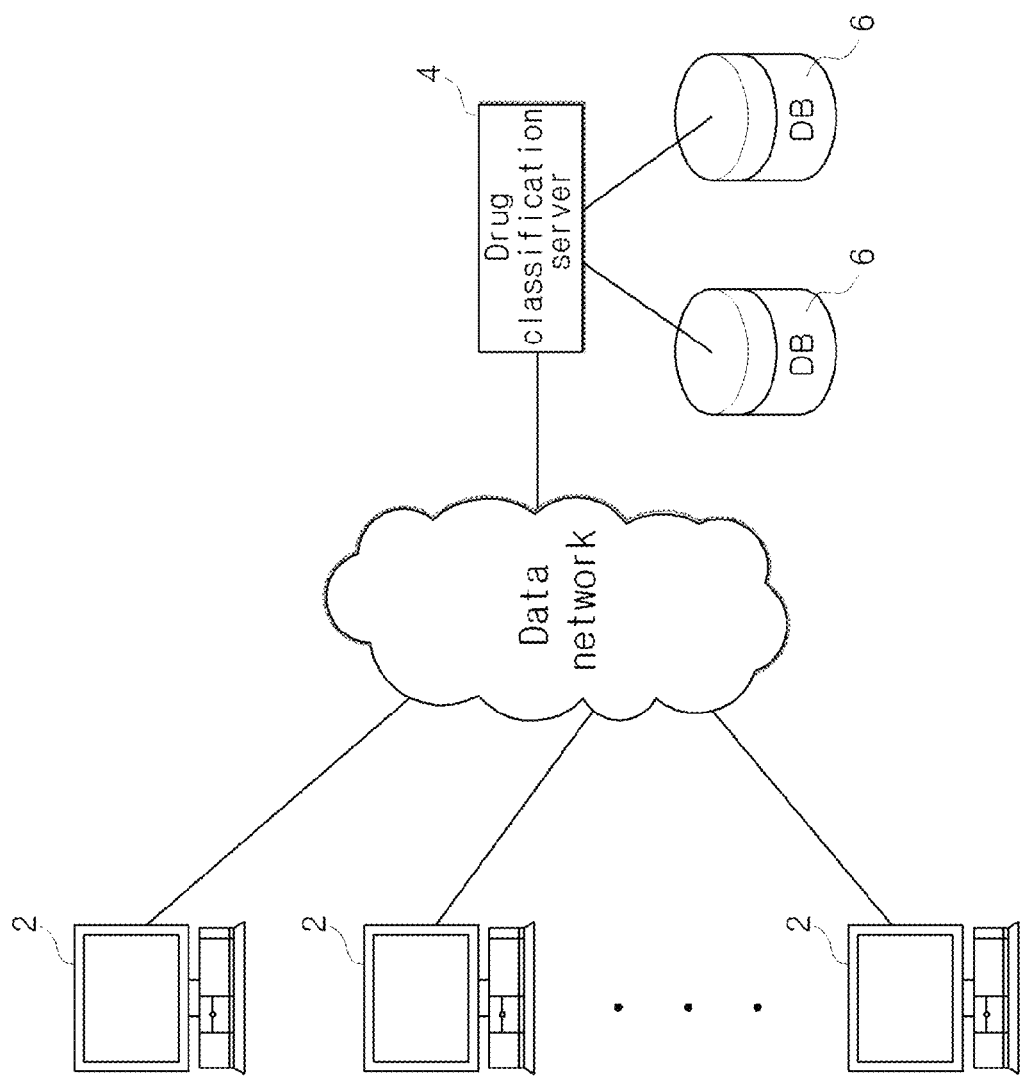
FIG. 1 is a schematic view illustrating a drug classification system using a generic group code and a universal drug number according to an exemplary embodiment of the present invention.

FIG. 1 is a schematic view illustrating a configuration of a drug classification system using a generic group code and a universal drug number according to an exemplary embodiment of the present invention.

Such a drug classification system has various performances, for example: determination of whether a drug comprises a single component or a composite formulation using a generic group code of the drug during classification and registration thereof; determination of an administration type, dose and formulation type of the drug; registration of a universal drug number corresponding to the code; tracing back the generic group code from the universal drug number; and identification of a company name and/or a trade name of the drug, so that individual drugs are easily and rapidly recognized.

More particularly, the drug classification system using a generic group code and a universal drug number according to the embodiment of the present invention has a user equipment 2 that connects to a drug classification server 4 through a data network, displays an information in association with generic group codes, which are pre-registered in the server by applying known generic group codes and/or universal drug numbers, displays detailed drug names in associated with the known generic group codes or, otherwise, inputs a specific drug name into the server in order to display corresponding generic group codes and universal drug numbers.

In this case, a user may include pharmacist/physician/pharmaceutical company who wish to obtain drug information including, for example: constitutional components of a drug, dose, administration type and/or formulation type thereof, and the like. That is, if the user is a pharmacist, the user equipment 2 may be a cell phone, a personal digital assistant (PDA), a personal computer, a pharmacy server and/or network, and so forth.

The drug classification system using a generic group code and a universal drug number according to the inventive embodiment also has a drug classification server 4 that automatically assigns a generic group code and a universal drug number corresponding to a new drug information, registers the assigned generic group code and universal drug number corresponding to the drug information, combines a company code into the universal drug number, receives an information regarding a certain generic group code, a certain universal drug number or a certain drug name, and then, extracts a corresponding information from the registered drug-related information, and transmits the extracted information to the user equipment 2; as well as a database 6 to store drug-related information.

Here, the foregoing generic group code is a nine-digit code registered in the drug classification server 4 in order to determine whether a drug comprises a single component or a composite formulation and, in addition, to identify the administration type, dose and/or formulation type of the drug.

The foregoing universal drug number registered in the drug classification server 4 is an inherent serial number associated with the corresponding generic group code. Therefore, if two or more drugs have the same universal drug number, these also have the same generic group code.

The drug classification server 4 is associated with a cable/radio telecommunication module, that is, a web server or a WAP server including a control part, RAMs, ROMs, a data interface, a database, etc., and is generally constructed using a typical personal computer or a workstation.

Such a data network sends/receives cable or radio data between the user equipment 2 and the drug classification server 4 and a concept of the network includes a wide range of cable/radio connection networks such as a public switched telephone network (PSTN), a mobile network, etc.

Figure 2:
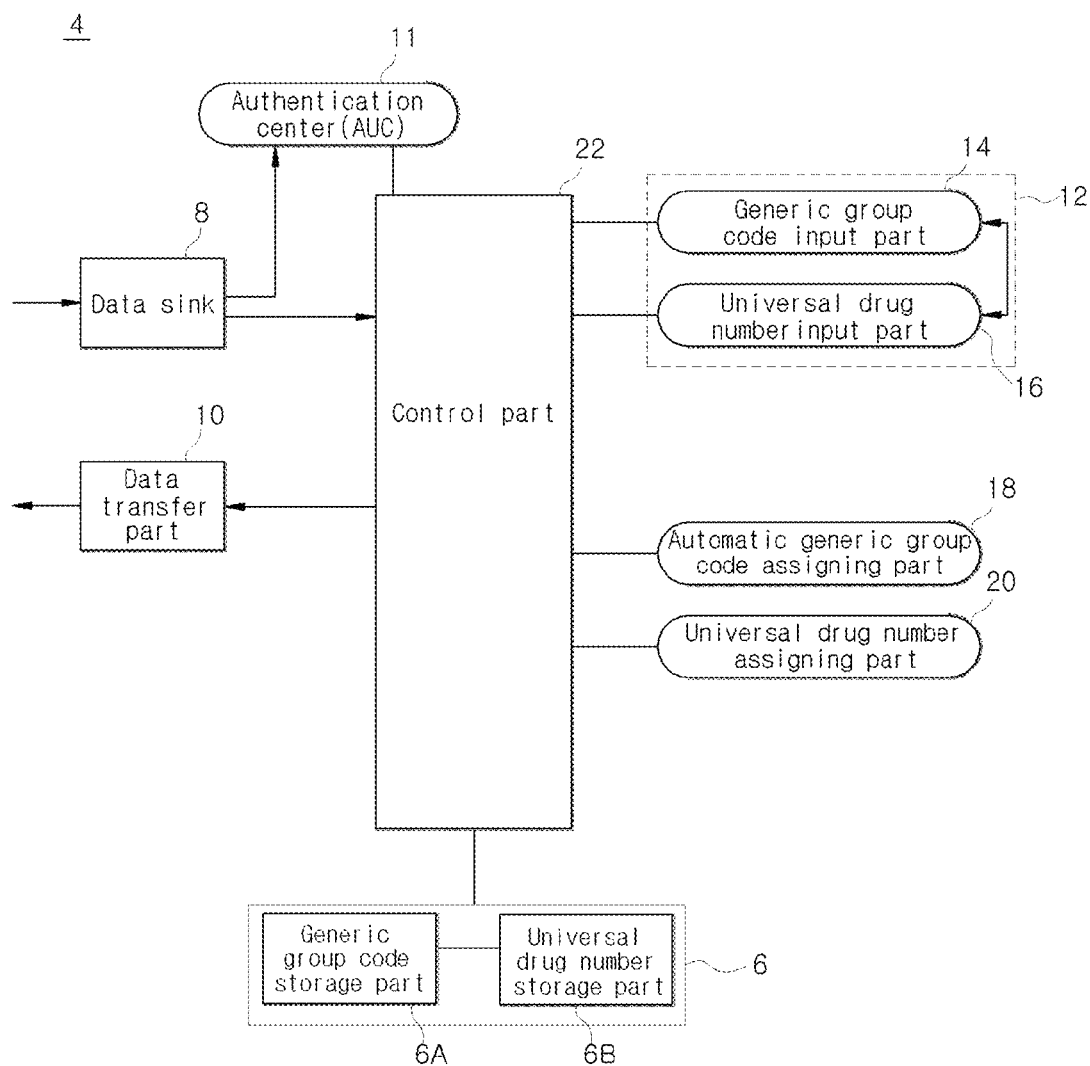
FIG. 2 is a block diagram illustrating a drug classification server included in the drug classification system using a generic group code and a universal drug number according to an exemplary embodiment of the present invention.

FIG. 2 is a block diagram illustrating a configuration of a drug classification server included in the drug classification system using a generic group code and a universal drug number according to an exemplary embodiment of the present invention.

Referring to FIG. 2, the drug classification server installed in the drug classification system according to the inventive embodiment consists of a data sink, a data transfer part, an AUC, a drug information registry, a generic group code input part, a universal drug number input part, an automatic generic group code assigning part, a universal drug number assigning part, a database and a control part.

A reference numeral 8 designates the data sink to receive information about generic group codes, universal drug numbers and/or drug names, as well as authentication information from the user equipment 2.

A reference numeral 10 represents the data transfer part that extracts drug information corresponding to a generic group code, universal drug number or drug name received from the user equipment 2, then, transmits the extracted information to the user equipment 2. A reference numeral 11 is an authentication center (AUC) to verify identity of a user according to the identification information received from the user equipment 2.

A reference numeral 12 refers to a drug information registry for newly registering a drug information, which is received from a key input part (not shown) connected to a drug classification server 4, to a database in order to view (or read) the information; a reference numeral 14 represents a generic group code input part installed in the drug information registry 12 to receive overall drug information including an information about a single component or composite formulation type drug; and a reference numeral 16 is a universal drug number input part installed in the drug information registry 12 to receive a universal drug number in association with a generic group code for the single component or composite formulation type drug.

A server manager may input a universal drug number into the foregoing universal drug number input part 16 in manual mode or, otherwise, a serial number for the universal drug number may be automatically inputted according to determination of whether a drug comprises a single component or a composite formulation. If two or more drugs comprise the same component, the same drug number is matched to the drugs. Only for a new component, a new universal drug number is automatically assigned.

A reference numeral 18 designates an automatic generic group code assigning part that automatically assigns a head rank information of the generic group code, depending on the single component or composite formulation type drug, from a new component information when this component information is inputted by the generic group code input part 14, then, combines the assigned information with a following rank information of the generic group code, which is pre-inputted, in order to automatically create a new unique generic group code.

The foregoing code assigning part 18 may determine whether the drug comprises a singe component or a composite formulation when the component information is inputted by the code input part 14, and then, assign a correct code to the single component drug or the composite formulation type drug.

For this reason, the code assigning part 18 is preferably divided into a single component code assigning part and a composite formulation code assigning part, which will be described in detail later.

A reference numeral 20 designates a universal drug number assigning part that creates a universal drug number matching to the unique generic group code, when the unique generic group code is newly created by the automatic generic group code assigning part 18. Since the number assigning part 20 creates a five-digit component number, the universal drug number is completed as a nine-digit number by aligning a company code made of four digits before this five-digit number.

A reference numeral 6 means a database to store generic group code information in association with corresponding universal drug number information, in which a generic group code storage part 6A and a universal drug number storage part 6B are provided. A reference numeral 22 designates a control part that operates individual processors installed in the drug classification server 4 which in turn controls drug information, creation of new generic group codes, and creation of new universal drug numbers and/or registration thereof FIG. 3 is a phase diagram illustrating a process of assigning a generic group code by the drug classification system using a generic group code and a universal drug number according to an exemplary embodiment of the present invention; and FIG. 4 shows web screens displaying interconnection outputs of generic group codes and universal drug numbers by the drug classification system using a generic group code and a universal drug number according to an exemplary embodiment of the present invention.

Figure 3:
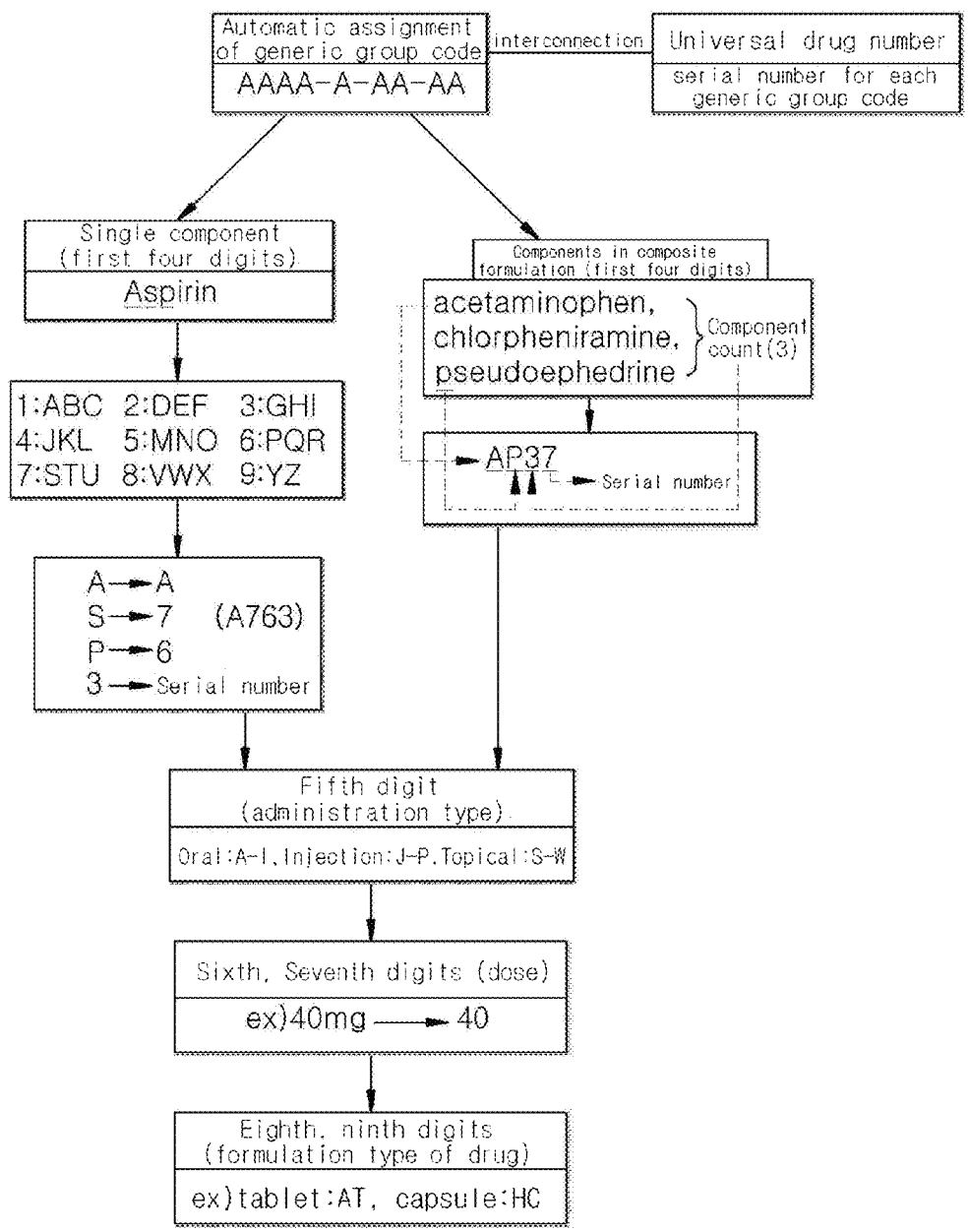
FIG. 3 is a phase diagram illustrating a process of assigning a generic group code by the drug classification system using a generic group code and a universal drug number according to an exemplary embodiment of the present invention.

Referring to the foregoing drawings, the generic group code information registered and viewed through the inventive drug classification system is completed into a nine-digit code (e.g., AAAA-A-AA-AA) as shown in FIG. 3.

The drug classification server 4 included in the drug classification system according to the inventive embodiment may directly receive a drug information manually selected according to whether a drug comprises a single component or a composite formulation or, otherwise, may automatically determine whether the drug comprises a single component or a composite formulation by directly inputting the drug information (e.g., Aspirin), thus driving a corresponding generic group code assigning processor.

The foregoing code assigning processor is the automatic code assigning part 18 illustrated in FIG. 2, in order to endow a generic group code to a drug in different manners for a single component and a composite formulation, respectively.

For a single component type drug, for example, with a component name of "Aspirin", the code assigning processor forms a first digit of the code by selecting the first alphabet (e.g., "A") of the component name.

Next, second and third digits of the code are designated with second and third alphabets of the component name. In other word, as illustrated in FIG. 3, alphabets from A to Z are converted and sorted into numerals. For instance, since the second alphabet of "Aspirin" is "S", the processor aligns "7" in the second digit of the code using a table in the FIG. 3.

Likewise, the third alphabet of "Aspirin" is "P" and the processor aligns "6" in the third digit of the code using the table in FIG. 3.

As described above, the first digit of the generic group code for a drug is assigned with the first digit alphabet extracted from the component name of the drug while the second and third digits of the same code are filled with numeral codes converted from alphabets corresponding to the second and third digits of the component name.

In this case, after collecting all of drugs with the same code from the first to third digits thereof, serial numbers are given to these drugs. Following this, the drug classification server 4 extracts component names of single component type drugs using a four-digit code included in the generic group code of each drug. Therefore, a user can recognize constitutional components of the drugs.

If a drug comprises a composite formulation and the composite formulation is composed of "acetaminophen, chlorpheniramine, pseudoephedrine," the code assigning processor forms the first digit of the generic group code for the drug by selecting a first alphabet of the first component (acetaminophen) (e.g., "A").

Then, the processor selects a first alphabet of the last component (pseudoephedrine) (e.g., "p") and forms the second digit of the generic group code for the drug. In this case, for the composite formulation drug, first digit alphabets in names of separate components must be sequentially inputted. For instance, where a manager registers a new composite formulation type drug composed of "acetaminophen, chlorpheniramine and psedoephedrine" in the drug classification server 4, first alphabets in names of three components are inputted in order such as "a→c→p."

Then, the code assigning processor also assigns the number of components contained in the composite formulation type drug to the third digit of the generic group code for the drug. For a composite formulation type drug as illustrated in FIG. 3, the drug comprises three different components and the third digit of the code becomes "3." If a drug contains more than 10 components, it is preferable to designate the numeral 10 as the alphabet "A," the numeral 11 as the alphabet "B", etc., which in turn prevents the number of digits from being altered.

Similar to the single component drug, after collecting all of drugs with the same code from the first to third digits thereof, serial numbers are given to these drugs (e.g., "7" illustrated in FIG. 3). Following this, the drug classification server 4 effectively and uniquely classifies the drugs using inherent names thereof with reference to a four-digit code included in the generic group code of each drug.

Although about 1,000 new drug names and/or trade names are now introduced every month, the number of new drugs comprising novel components is only up to about 20 each year. Therefore, these drugs are effectively subjected to assignment of generic group codes for drug classification.

According to whether a second digit of the generic group code for a given drug is an alphabet or a numeral, it is easily recognized whether the drug comprises a single component or a composite formulation.

For instance, if a generic group code is "F765A40AT," the second digit is the numeral ("7") and the drug with the code is easily recognized as a single component type drug. On the other hand, for a generic group code of "AP37A30HC", the drug with the code (having the second digit of alphabet "P") may be a composite formulation type drug.

However, provided that an amino acid formulation starts "W" as the first alphabet, a vitamin formulation starts "V" as the first alphabet and an isotope formulation starts "Y" as the first alphabet during drug classification, although these are all the composite formulation type drugs.

The fifth digit of the generic group code represents an administration type of the drug, as illustrated in FIG. 3. "A" to "I" are assigned to oral administration drugs, "J" to "P" are assigned to injecting drugs, and "S" to "W" are assigned to topical medicaments.

For example, a drug with "A" in the fifth digit of the code thereof is easily recognized as an oral administration drug. Such an administration type should be directly inputted into the drug classification server 4 by a manager who is responsible for registration of novel drugs.

The sixth and seventh digits of the generic group code represent a dose of the drug, as illustrated in FIG. 3. For example, these digits together represent "40," meaning that a dose of the drug is "40 mg." Such a dose related code should also be inputted into the drug classification server by the responsible manager.

Lastly, the eighth and ninth digits of the generic group code together represent a formulation type of the drug, as illustrated in FIG. 3. "AT" is assigned to a tablet, "HC" is assigned to a capsule, and other two-digit alphabets are also assigned to corresponding formulation types of the drugs. As described above, such a formulation type related code should be inputted into the drug classification server by the responsible manager.

As a result, a complete nine-digit code is endowed to a drug as the generic group code by the drug classification system using a generic group code and a universal drug number according to an exemplary embodiment of the present invention. The nine-digit code is useful for managing characteristics of the drug in view of constitutional ingredients thereof and beneficial features of the nine-digit code are listed as follows:

1. In preparation of a document (such as prescription), a long component name occupying a large space in the document is abbreviated into nine digits and clearly expressed which in turn is helpful for message or knowledge transfer (a main component code system commonly used in the art does not substantially include codes for vitamins and, although amino acid formulations are included therein, does not specifically classify or sort the formulations in terms of constitutional ingredients thereof).

2. For drugs comprising the same component, the first four digits of generic group codes thereof are substantially equal. Therefore, these drugs are easily comparable.

3. About 50,000 medicaments are managed with 13,000 generic group codes, thus effectively reducing a management capacity for substances stored in a database and conveniently managing the same.

4. When a patient wishes to have information, data may be easily searched only using a known generic group code (no practical assignment of generic group codes to all of drugs and/or medicines was known before the present invention).

5. With regard to management of interaction between drugs, prohibition of simultaneous uses of injection drugs, prohibition of administration to pregnant woman, instruction for administration of medicines, etc., a quantity of goods under management is decreased if the management is executed in association with generic group codes of the goods rather than the goods, thus reducing workload to about one-third of the original work.

6. The drugs may be statistically managed in terms of constitutional components thereof. The statistical management is also preferably performed for composite formulation type drugs.

Meanwhile, the drug classification system using a generic group code and a universal drug number according to an exemplary embodiment of the present invention may assign a universal drug number to a certain drug, wherein the universal drug number is completed by adding an inherent five-digit serial number to the generic group code which was assigned beforehand.

That is, if two or more drugs have the same five-digit serial number, these also have the same generic group code.

The universal drug number assigned by the drug classification system of the inventive embodiment is completed into a nine-digit number having four digits as a company code and the remaining five digits expressing the five-digit serial number for the drug.

For instance, as illustrated in lower part of FIG. 4, if Daewon Pharmaceutical Co., Ltd. has a company code of "1631" and a serial number matching to a generic group code of a particular drug is "41533," the drug has a complete universal drug number in nine digits such as, 163141533, by combining the above company code with the five-digit serial number.

Here, according to the drug classification system of the inventive embodiment, the drug classification server 4 has a number of generic group codes and corresponding universal drug numbers stored in a database. As illustrated in FIG. 4, "furosemide 40 mg Tab" is represented by a generic group code "F765A40AT" and, in addition, has a component number "41533" in association with the corresponding generic group code. Although characteristics of a drug is hardly identified with numerals, the drug classification server 4 can connect such numerals to a particular generic group code which in turn easily accesses to drug information related thereto.

For instance, if a user accesses to the drug classification server 4 through a user equipment 2 and clicks the generic group code "F765A40AT" while displaying an upper table in FIG. 4 on a screen, a lower table in FIG. 4 is outputted and displayed. In the lower table of FIG. 4, a plurality of goods with the same generic group code "FT765A40AT" produced by different manufacturers are displayed.

The nine-digit universal drug number contributes to smooth and favorable transfer and exchange of drug information, and beneficial features of the nine-digit number are listed as follows:

1. In preparation of a document, a long component name occupying a large space of the document is abbreviated into five digits and clearly expressed which in turn is helpful for message or knowledge transfer.

2. Although the generic group code has restriction in representing a trade name of a medicament produced by a particular manufacturer, the nine-digit number having a company code in four digits may clearly indicate the trade name as well as the company name (e.g., for UDN9:4647-41533, the company is Handok Pharmaceutical Co., Ltd. which is identified from the first four digits as the company code while the trade name is "LASIX TABS" identified from the following five digits).

3. The universal drug number indicates the drug name in a medical prescription.

4. Even a patient without knowledge of drug names may recognize information of a drug and understand side effects thereof from the five-digit component number (like a tail-tag of the drug).

5. A clinic and/or pharmacy may give an order with a medicine wholesaler through an electronic order system.

The following description will be given for functions and effects of the drug classification system using a generic group code and a universal drug number according to an exemplary embodiment of the present invention, taken in conjunction with the accompanying drawings.

Figure 5:
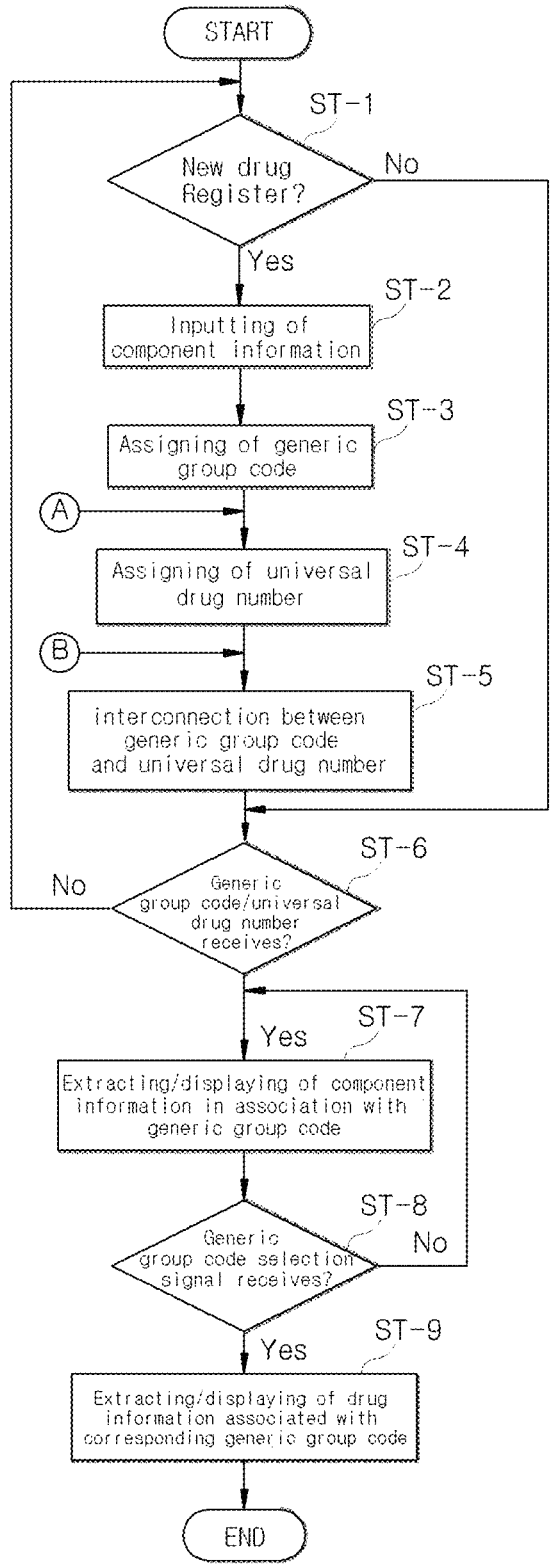
FIG. 5 is a flow chart illustrating a signal flow of the drug classification system using a generic group code and a universal drug number according to an exemplary embodiment of the present invention.

FIG. 5 is a flow chart illustrating a signal flow of the drug classification system using a generic group code and a universal drug number according to an exemplary embodiment of the present invention.

First, when a responsible manager registers a new drug in the drug classification server 4 included in the drug classification system according to the inventive embodiment, component information is inputted.

Then, a generic group code corresponding to the component information is assigned.

After assignment of the generic group code, a universal drug number matching to the generic group code is assigned.

After assignment of the universal drug number, the drug classification server 4 processes both the generic group code and the universal drug number to enable interconnection there between.

If the user equipment 2 connects to the drug classification server 4 and inputs a certain generic group code, universal drug number or trade name into the server, the server 4 extracts component information in association with the inputted generic group code, universal drug number or trade name and displays the extracted result on the user equipment 2.

Then, the drug classification server 4 determines whether a signal for selecting the generic group code is received from the user equipment 2 or not and, if so, extracts a drug information in association with the generic group code and displays the extracted result on the user equipment 2.

The extracted drug information is illustrated in the lower table of FIG. 4 wherein trade names, coverage and/or non-coverage, formulation type, price, registered date, etc. are included in the drug information.

Figure 6:
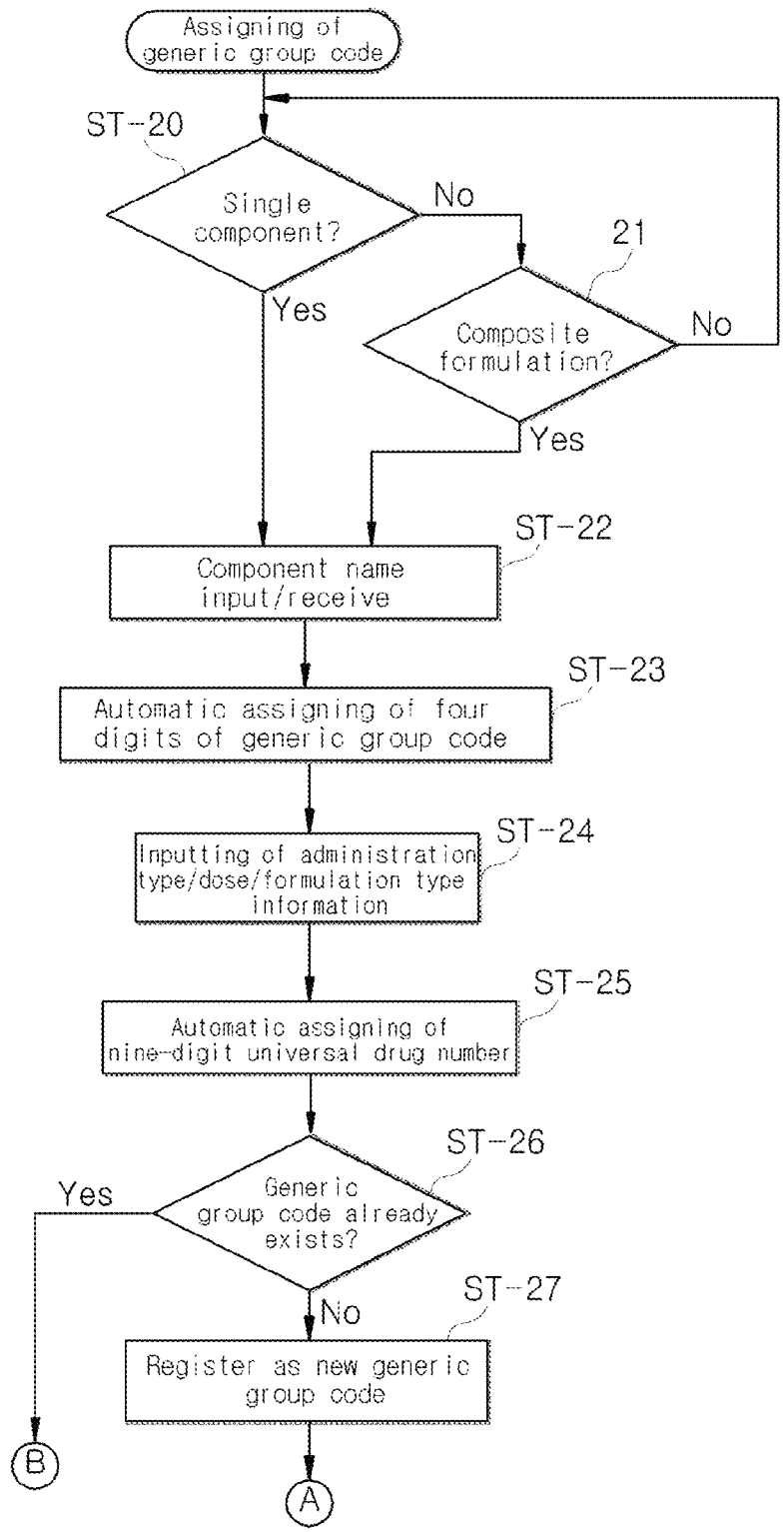
FIG. 6 is a flow chart illustrating a process of registering a drug among the signal flow of the drug classification system using a generic group code and a universal drug number according to an exemplary embodiment of the present invention.

FIG. 6 is a flow chart illustrating a process of registering a drug among the signal flow of the drug classification system using a generic group code and a universal drug number according to an exemplary embodiment of the present invention.

First, according to the drug classification system of the inventive embodiment, a process for registration of a drug is executed by the drug classification server 4. A responsible manager may directly select a single component drug or a composite formulation type drug to be registered or, otherwise, the drug classification server 4 may automatically determine whether the drug is a single component drug or a composite formulation type drug. When the manager selects the single component drug or the composite formulation type drug, the drug classification server 4 is driven one registration processor or the other processor according to the selection.

If the manager inputs a component name, the drug classification server 4 registers the component name and automatically assigns a four-digit code corresponding to the first four digits of a generic group code.

Next, when information about administration type, dose and formulation type is inputted by the manager, the drug classification server 4 automatically combines the inputted information with the foregoing assigned code to complete the generic group code.

Following this, the drug classification servers determines whether the above assigned generic group code already exists in the server or not. If the assigned generic group code is not present in the server, the server registers the assigned generic group code as a new generic group code. Otherwise, if the assigned generic group code already exists in the server, the server registers the assigned group code in association with the universal drug number having the company code combined therein.

While a drug classification system using a generic group code and a universal drug number and a drug classification method of the present invention have been described with reference to exemplary embodiments, various modifications and variations to the present invention may be practiced by those skilled in the part, without departing from the spirit and scope of the present invention as defined by the appended claims.

What is claimed is:

1. A drug classification system, comprising:
at least one user equipment; and
a drug classification server computer creating a nine-digit code for registering a new drug, the drug classification server computer connected through a data network, the drug classification server computer comprising a code assigning processor, the code assigning processor creating a first four-digit code of the nine-digit by performing the following steps in response to determining whether the drug has a single ingredient: assigning the first (1) digit by selecting the first alphabet letter of the drug name, assigning the second (2) digit by selecting a numeral corresponding to the second alphabet letter of the drug name based on a lookup table, assigning the third (3) digit by selecting a numeral corresponding to the third alphabet letter of the drug name based on the lookup table, and assigning the fourth (4) digit by selecting a serial number, the code assigning processor creating a first four digit code of the nine-digit by performing the following steps in response to determining whether the drug has multiple ingredients: assigning the first (1) digit by selecting the first alphabet letter of the first ingredient name, assigning the second (2) digit by selecting the first alphabet letter of the last ingredient name, assigning the third (3) digit by selecting a numeral corresponding to a total number of the multiple ingredients, and assigning the fourth (4) digit by selecting a serial number, the code assigning processor creating a last five-digit code of the nine-digit by performing the following: assigning the fifth (5) digit by selecting one letter code representing an administration type of the drug, assigning the sixth (6) digit and the seventh (7) digit by selecting a numeral code representing a dosage of the drug, and assigning the eighth (8) digit and the ninth (9) digit by selecting a two-letter code representing a formulation type of the drug, the at least one user equipment displaying an information in association with the nine-digit code through the data network.

2. The system according to claim 1, wherein the drug classification server computer further comprises: a data sink to receive information about generic group codes, universal drug numbers and/or drug names as well as authentication information from the at least one user equipment; a data transfer part that extracts drug information corresponding to a generic group code, universal drug number or drug name received from the at least one user equipment, then, transmits the extracted information to the at least one user equipment; an AUC to verify identity of a user according to the identification information received from the at least one user equipment; a drug information registry for newly registering a drug information, which is received from a key input part connected to the drug classification server computer; a generic group code input part installed in the drug information registry to receive overall drug information including an information about a single ingredient or multiple ingredient type drug; a universal drug number input part installed in the drug information registry to receive a universal drug number in association with a generic group code for the single ingredient or multiple ingredient type drug; a universal drug number assigning part that creates a universal drug number matching to the unique generic group code, when the unique generic group code is newly created and completed as a nine-digit number by aligning a company code made of four digits before this five-digit number; a database to store generic group code information in association with corresponding universal drug number information, in which a generic group code storage part and a universal drug number storage part are provided; and a control part that operates individual processors installed in the drug classification server computer which in turn controls drug information, creation of new generic group codes, and creation of new universal drug numbers and/or registration thereof.

3. The system according to claim 1, wherein the drug classification server computer further comprises: a server manager that inputs a universal drug number into the universal drug number input part in manual mode or, otherwise, a serial number for the universal drug number is automatically inputted according to determination of whether a drug comprises a single ingredient or a multiple ingredient formulation, and if two or more drugs comprise the same ingredient, then the same drug number is matched to the drugs, else if only for a new ingredient, then a new universal drug number is automatically assigned.

4. The system according to claim 1, wherein the lookup table lists followings:
1: ABC, 2: DEF, 3: GHI, 4: JKL, 5: MNO, 6: PQR, 7: STU, 8: VWX, and 9: YZ.

5. The system according to claim 1, wherein the at least one user equipment connects to the drug classification server computer through the network, displays an information in association with generic group codes, which are pre-registered in the server by applying known generic group codes and/or universal drug numbers, displays detailed drug names in associated with the known generic group codes or, otherwise, inputs a specific drug name into the server in order to display corresponding generic group codes and universal drug numbers.

6. The system according to claim 5, wherein if the user is a pharmacist, then the at least one user equipment is a cell phone, a personal digital assistant (PDA), a personal computer, or a pharmacy server and/or network.

7. A drug classification system, comprising: a drug classification server computer that automatically assigns a nine-digit generic group code and a universal drug number corresponding to a new drug information by creating a first four-digit code of the nine-digit by performing the following steps in response to determining whether the drug has a single ingredient: assigning the first (1) digit by selecting the first alphabet letter of the drug name, assigning the second (2) digit by selecting a numeral corresponding to the second alphabet letter of the drug name based on a lookup table, assigning the third (3) digit by selecting a numeral corresponding to the third alphabet letter of the drug name based on the lookup table, and assigning the fourth (4) digit by selecting a serial number, or creating a first four digit code of the nine-digit by performing the following steps in response to determining whether the drug has multiple ingredients: assigning the first (1) digit by selecting the first alphabet letter of the first ingredient name, assigning the second (2) digit by selecting the first alphabet letter of the last ingredient name, assigning the third (3) digit by selecting a numeral corresponding to a total number of the multiple ingredients, and assigning the fourth (4) digit by selecting a serial number, and creating a last five-digit code of the nine-digit by performing the following: assigning the fifth (5) digit by selecting one letter code representing an administration type of the drug, assigning the sixth (6) digit and the seventh (7) digit by selecting a numeral code representing a dosage of the drug, and assigning the eighth (8) digit and the ninth (9) digit by selecting a two-letter code representing a formulation type of the drug, registers the assigned generic group code and universal drug number corresponding to the drug information, combines a drug company code into the universal drug number, receives an information regarding a certain generic group code, a certain universal drug number or a certain drug name, and then, extracts a corresponding information from registered drug-related information, and transmits the extracted information to an user equipment through a data network as well as a database to store drug-related information.

8. The drug classification system according to claim 7, wherein the universal drug number registered in the drug classification server computer is an inherent serial number associated with the corresponding generic group code, so that if two or more drugs have the same universal drug number, then these also have the same generic group code.

9. The drug classification system according to claim 7, wherein the drug classification server computer is associated with a cable/radio telecommunication module comprising a web server or a WAP server including a control part, RAMs, ROMs, a data interface, a database, and is constructed using a personal computer or a workstation.

10. The drug classification system according to claim 7, wherein the data network sends/receives cable or radio data between the user equipment and the drug classification server computer, and includes a public switched telephone network (PSTN), or a mobile network.

11. A nine-digit drug classification method for registering a new drug, comprising the following steps of:
creating, by a drug classification server computer, a first four-digit code of the nine-digit by performing the following steps in response to determining whether the drug has a single ingredient: assigning the first (1) digit by selecting the first alphabet letter of the drug name, assigning the second (2) digit by selecting a numeral corresponding to the second alphabet letter of the drug name based on a lookup table, assigning the third (3) digit by selecting a numeral corresponding to the third alphabet letter of the drug name based on the lookup table, and assigning the fourth (4) digit by selecting a serial number;
creating, by the drug classification server computer, a first four digit code of the nine-digit by performing the following steps in response to determining whether the drug has multiple ingredients: assigning the first (1) digit by selecting the first alphabet letter of the first ingredient name, assigning the second (2) digit by selecting the first alphabet letter of the last ingredient name, assigning the third (3) digit by selecting a numeral corresponding to a total number of the multiple ingredients, and assigning the fourth (4) digit by selecting a serial number;
creating, by the drug classification server computer, a last five-digit code of the nine-digit by performing the following: assigning the fifth (5) digit by selecting one letter code representing an administration type of the drug, assigning the sixth (6) digit and the seventh (7) digit by selecting a numeral code representing a dosage of the drug, and assigning the eighth (8) digit and the ninth (9) digit by selecting a two-letter code representing a formulation type of the drug; and
transmitting the nine-digit code's information to an user equipment over a data network.

12. The nine-digit drug classification method according to claim 11, wherein the lookup table lists followings: 1: ABC, 2: DEF, 3: GHI, 4: JKL, 5: MNO, 6: PQR, 7: STU, 8: VWX, and 9: YZ.

* * * * *